United States Patent [19]

Avar

[11] Patent Number: 4,774,332

[45] Date of Patent: Sep. 27, 1988

[54] PIPERIDINE CONTAINING STABILIZER COMPOUNDS

[75] Inventor: Lajos Avar, Biel-Benken, Switzerland

[73] Assignee: Sandoz, Ltd., Basel, Switzerland

[21] Appl. No.: 884,587

[22] Filed: Jul. 11, 1986

Related U.S. Application Data

[63] Continuation-in-part of Ser. No. 764,865, Aug. 12, 1985, abandoned.

[30] Foreign Application Priority Data

Aug. 14, 1984 [DE] Fed. Rep. of Germany ....... 3429826

[51] Int. Cl.$^4$ ................. C07D 521/00; C07D 401/14; C07D 401/02; C07D 413/02
[52] U.S. Cl. ......................................... 544/70; 546/16; 546/19; 546/20; 546/188; 546/189; 546/242; 546/244; 546/245; 524/96; 524/102; 524/103
[58] Field of Search ................... 546/16, 19, 20, 188, 546/189, 242, 244, 245; 544/70

[56] References Cited

U.S. PATENT DOCUMENTS

| | | | |
|---|---|---|---|
| 3,982,006 | 9/1976 | Hall | 514/329 |
| 4,110,304 | 8/1978 | Gilg et al. | 546/16 |
| 4,344,877 | 8/1982 | Nikles et al. | 546/188 |
| 4,426,471 | 1/1984 | Berner | 524/91 |
| 4,426,472 | 1/1984 | Berner | 524/99 |

FOREIGN PATENT DOCUMENTS 1196444  11/1983  Canada ................................. 546/20

Primary Examiner—Robert T. Bond
Attorney, Agent, or Firm—Gerald D. Sharkin; Richard E. Vila; Thomas C. Doyle

[57] ABSTRACT

A compopund containing one or more units of formula I

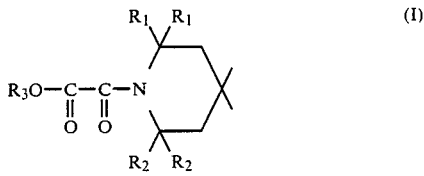

in which $R_1$ is —$CH_2C_{1-4}$alkyl or —$CH_3$ or both groups $R_1$ form —$(CH_2)_5$—;

$R_2$ is —$CH_2C_{1-4}$alkyl or —$CH_3$ or both groups $R_2$ form —$(CH_2)_5$—;

$R_3$ is furylmethyl, unsubstituted $C_{1-18}$alkyl; $C_{1-4}$alkyl monosubstituted by phenyl, the phenyl group of which is unsubstituted or substituted by 1 to 3 groups selected from —OH and $C_{1-8}$alkyl; $C_{2-8}$alkyl monosubstituted by $C_{1-4}$alkoxy; phenyl, unsubstituted or substituted by 1 to 3 groups selected from $C_{1-8}$alkyl and —OH; or cyclohexy, unsubstituted or monosubstituted by $C_{1-8}$alkyl or —OH.

These compounds are useful as light stabilizers for polymeric material.

33 Claims, No Drawings

PIPERIDINE CONTAINING STABILIZER COMPOUNDS

This application is a continuation-in-part of our co-pending application Serial No. 764,865, filed Aug. 12, 1985, now abandoned.

The invention relates to N-substituted tetraalkyl-piperidine compounds, useful as light stabilisers for polymeric materials.

According to the invention there is provided a light stabiliser for polymeric materials comprising a compound containing one or more units of formula I

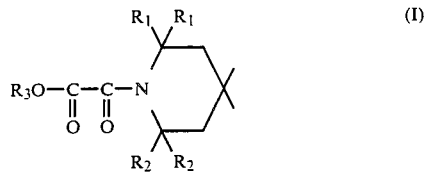

in which
$R_1$ is —$CH_2C_{1-4}$alkyl or —$CH_3$ or both groups $R_1$ form —$(CH_2)_5$—;
$R_2$ is —$CH_2C_{1-4}$alkyl or —$CH_3$ or both groups $R_2$ form —$(CH_2)_5$—;
$R_3$ is furylmethyl, unsubstituted $C_{1-18}$alkyl; $C_{1-4}$alkyl monosubstituted by phenyl, the phenyl group of which is unsubstituted or substituted by 1 to 3 groups selected from —OH and $C_{1-8}$alkyl; $C_{2-8}$alkyl monosubstituted by $C_{1-4}$alkoxy; phenyl, unsubstituted or substituted by 1 to 3 groups selected from $C_{1-8}$alkyl and —OH; or cyclohexyl, unsubstituted or monosubstituted by $C_{1-8}$alkyl or —OH.

Preferably the compound of formula I is of formula I'

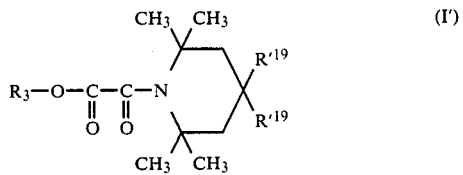

in which each $R_{19}$ independently, is hydrogen or an organic radical or both groups $R_{19}$ together with the C-atom to which they are attached form a cyclic organic radical.

In this Specification where a significance appears more than once in a formula its significances are independent of one another unless indicated to the contrary. All alkyl groups (containing more than 2 carbon atoms) and all alkenyl groups (containing more than 2 carbon atoms) are linear or branched.

Preferably $R_1$ and $R_2$ are all —$CH_3$.

Preferably $R_3$ is $C_{1-14}$alkyl, phenyl or benzyl, more preferably $C_{1-4}$alkyl, most preferably $C_{1-2}$alkyl.

Preferred compounds containing one or more units of formula I are of formula II

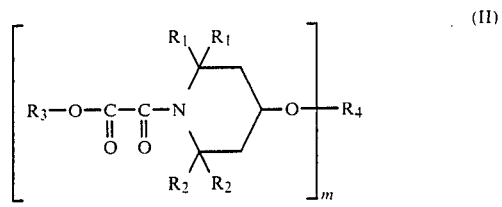

in which
$R_1$, $R_2$ and $R_3$ are as defined above;
m is 1, 2, 3 or 4; and
$R_4$, when m=1, is $C_{1-22}$alkyl; phenyl-$C_{1-4}$alkyl; $C_{1-4}$alkyl phenyl; $C_{1-21}$alkylcarbonyl; phenylcarbonyl; $C_{5-6}$cycloalkylcarbonyl; $C_{1-4}$alkyl-$C_{5-6}$cycloalkylcarbonyl; or phenyl $C_{1-6}$alkylcarbonyl in which the phenyl group of each phenyl-containing significance of $R_4$ can be substituted by 1 or 2 $C_{1-9}$alkyl groups and/or a hydroxyl group;
$R_4$, when m=2, is $C_{2-22}$alkylene; $C_{4-12}$alkenylene; xylylene; tolylene; phenylene or —CO—R—CO— where R is a direct bond, $C_{1-6}$alkylene, $C_{2-6}$alkenylene or phenylene unsubstituted or monosubstituted by $C_{1-4}$alkyl;
$R_4$, when m=3, is

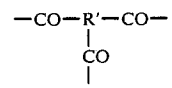

where R' is $C_{1-12}$alkanetriyl; and
$R_4$, when m=4, is $-(CO)_4R''$ where R'' is $C_{1-12}$alkanetetrayl.

Preferably m is 1 or 2, more preferably 1.

Preferably when m=1, $R_4$ is $R_4'$ where $R_4'$ is phenyl-carbonyl, t-butylphenylcarbonyl, p-t-butylphenyl, $C_{15-19}$alkylcarbonyl, 3,5-di-tert.-butyl-4-hydroxyphenylethyl or 3,5-di-t-butyl-4-hydroxyphenyl carbonyl or, when m=2, $-(CH_2)_8$.

Alternatively preferred compounds, containing one or more units of formula I, are of formula III

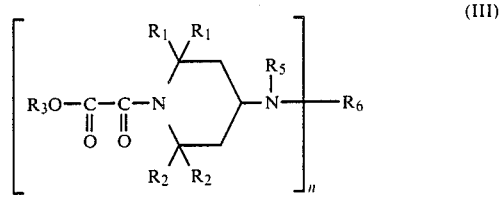

in which
$R_1$, $R_2$ and $R_3$ are defined above;
$R_5$ is hydrogen; $C_{1-2}$alkylcarbonyl; $C_{1-12}$alkyl; phenyl $C_{1-12}$alkyl, phenylcarbonyl or phenyl $C_{1-8}$alkylcarbonyl, in which the phenyl group of each phenyl-bearing $R_5$ group is unsubstituted or mono-substituted by —OH or $C_{1-9}$alkyl or the phenyl group is substituted by one —OH group and 1 or 2 $C_{1-4}$alkyl groups;
n is 1 or 2;
$R_6$, when n=1, is $C_{1-12}$alkyl; $C_{2-12}$alkenyl; $C_{5-6}$cycloalkyl or —$CH_2CH_2COOR_3$ where $R_3$ is as defined above; or
$R_6$, when n=2, is $C_{2-12}$alkylene, phenylene, xylylene or tolylene.

Preferably any phenyl group in $R_5$ is p-t-butylpheny, p-nonylphenyl, 3,5-di-t-butyl-4-hydroxyphenyl or unsubstituted phenyl.

Alternatively preferred compounds containing one or more units of formula I, are of formula IV

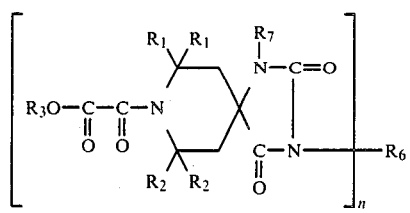

in which $R_1$ to $R_3$, $R_6$ and n are as defined above and $R_7$ is hydrogen or $C_{1-12}$alkyl.

Preferably $R_7$ is $R_7'$ where $R_7'$ is methyl or ethyl.

Alternatively preferred compounds containing one or more units of formula I are of formula V

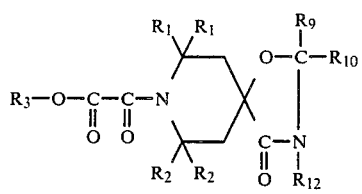

in which
$R_3$ is defined above;
$R_{12}$ is hydrogen or

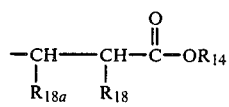

$R_{14}$ is hydrogen, a $C_{1-21}$alkyl or $C_{2-22}$alkenyl group which alkyl or alkenyl group may be unsubstituted or monosubstituted by phenyl or naphthyl and which alkyl or alkenyl group may be interrupted by —NH—, oxygen or by a $C_{1-4}$alkylimine group; phenyl; ($C_{1-12}$alkyl)phenyl; $C_{5-12}$cycloalkyl or $C_{2-20}$alkyl uninterrupted or interrupted by —NH— or oxygen or by a $C_{1-4}$alkylimine group and which alkyl group is substituted by 1 to 3 groups of formula (a) defined below and/or $C_{1-21}$alkylcarbonyloxy groups; or $C_{2-20}$alkenyl uninterrupted an interrupted by —NH— or oxygen or $C_{1-4}$alkylimine and which alkenyl group is substituted by 1 to 3 groups of formula (a) defined below

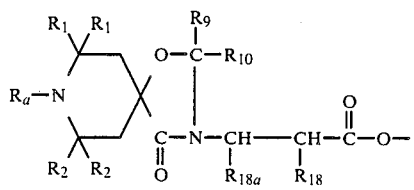

and/or $C_{1-21}$alkylcarbonyloxy groups;
where
$R_a$ is hydrogen, $C_{1-8}$alkyl,

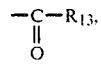

cyanomethyl or

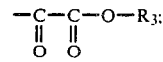

$R_{13}$ is $C_{1-6}$alkyl, phenyl, —O—$C_{1-4}$alkyl or —$NR_{15}R_{16}$;
$R_{15}$ is hydrogen, $C_{1-12}$alkyl, $C_{5-6}$cycloalkyl, phenyl or $C_{1-12}$alkyl phenyl;
$R_{16}$ has a significance of $R_{15}$ (independently of $R_{15}$) other than hydrogen; or
$R_{15}$ or $R_{16}$ together with the N-atom to which they are attached form a 5- to 7-membered ring that may contain an -O-atom additionally (preferably forming a piperidine or morpholine ring);
$R_{18}$ is hydrogen or methyl;
$R_{18a}$ is hydrogen, methyl, phenyl or

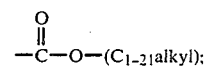

$R_9$ and $R_{10}$, independently of one another, are hydrogen, $C_{1-30}$alkyl or benzyl; or
$R_9$ is hydrogen or $C_{1-4}$alkyl and $R_{10}$ is phenyl, $C_{1-4}$alkylphenyl, chlorophenyl, 4-hydroxy-3,5-ditert.-butylphenyl or naphthyl; or
$R_9$ and $R_{10}$ together with the C-atom to which they are attached form a $C_{5-15}$cycloalkylidene ring unsubstituted or substituted by a $C_{1-4}$alkyl group or $R_9$ and $R_{10}$ together with the C-atom to which they are attached form a group of formula (b)

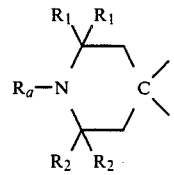

where $R_a$, $R_1$ and $R_2$ are defined above.

Preferably $R_9$ and $R_{10}$ together with the C-atom to which they are attached form a cyclic group. More preferably $R_9$ and $R_{10}$ together with the C-atom to which they are attached form cyclopentylidene, cyclohexylidene or cyclododecylidene, most preferably cyclododecylidene.

Preferably $R_{14}$ is $R_{14}'$ where $R_{14}'$ is $C_{1-12}$alkyl uninterrupted or interrupted by oxygen or an —NH— group, $C_{2-12}$alkenyl uninterrupted or interrupted by oxygen or —NH—, $C_{5-6}$cycloalkyl, phenyl $C_{1-4}$alkyl, phenyl or $C_{1-12}$alkylphenyl or a group of formula (c) to (1) below to whose free valencies further groups (a) and/or $C_{1-21}$alkylcarbonyloxy are attached.

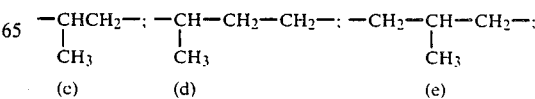

-continued

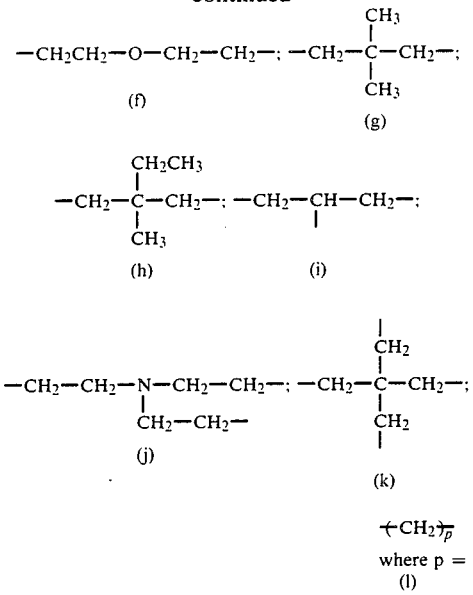

Compounds containing one or more units of formula I can be prepared by taking the corresponding N-unsubstituted compound containing groups of formula X

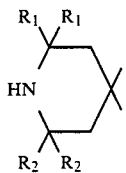

and reacting with a compound of formula XI

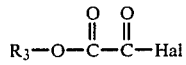

where $R_1$, $R_2$ and $R_3$ are as defined above and Hal is chloro or bromo, by known methods for amidation.

Compounds of formula (X) and (XI) are known or may be made from known compounds by known methods.

Further, according to the invention there is provided a polymeric composition comprising a polymeric material and a compound containing one or more units of formula I (hereinafter referred to as "compound(s) of formula I").

Compounds of formula I are useful as stabilizers to protect polymeric materials against degradation by light. The compounds have particularly good solubility and miscibility in solvent systems and in liquid polymers and prepolymers, which makes them useable in a wide range of polymeric materials.

The concentration of compound of formula I employed in the polymeric material is suitably 0.01 to 5% by weight, preferably 0.02 to 1% by weight. The compound may be added before, during or after the polymerization step, and may be added in solid form; in solution, preferably as a liquid concentrate containing from 20 to 80% by weight of compound of formula I; or as a solid masterbatch composition containing 20 to 80% by weight of compound of formula I and 80 to 20% by weight of a solid polymeric material which is identical with or compatible with the polymeric material to be stabilized.

Suitable polymeric materials include plastic materials for example polyethylene, polypropylene, ethylene/propylene copolymers, polyvinyl chloride, polyester; polyamide, polyurethane, polyacrylonitrile, ABS, terpolymers of acrylates, styrene and acrylonitrile, styrene/acrylonitrile and styrene/butadiene. Other plastics materials such as polybutylene, polystyrene, chlorinated polyethylene, polycarbonate, polymethylmethacrylate, polyphenylene oxide, polypropylene oxide, polyacetals, phenol/formaldehyde resins and epoxy resins may also be used. Preferred plastic materials are polypropylene, polyethylene, ethylene/propylene copolymers and ABS. Natural polymers for example natural rubber may also be stabilized, as may lubricating oils containing polymeric material.

The compounds of formula I may be incorporated by known methods into the polymeric material to be stabilized. Of particular importance is blending of the compounds with thermoplastic polymers in the melt, for example in a melt blender during the formation of shaped articles, including foils, films, tubes, containers, bottles, fibres and foams by extrusion, injection moulding, blow moulding, spinning or wire coating.

It is not essential for the polymeric material to be fully polymerised before mixing with the compounds according to the invention. The compounds may be mixed with monomer, prepolymer or precondensate, and the polymerisation or condensation reaction carried out subsequently. This will of course be the preferred method of incorporation of the compounds into thermosetting polymers, which cannot be melt blended.

The compounds of formula I may be used alone or in combination with other stabilizers, for example antioxidants. Examples include sterically hindered phenols, sulphur or phosphorus-containing compounds or mixtures of these. Examples are benzofuran-2-ones; indolin-2-ones and sterically hindered phenols such as β-(4-hydroxy-3,5-ditert.-butylphenyl)-propionyl stearate, methane tetrakis-(methylene-3(3′,5′-ditert.-butyl-4-hydroxyphenyl-)-propionate], 1,3,3-tris-(2-methyl-4-hydroxy-5-tert.-butylphenyl)-butane, 1,3,5-tris(4-tert.-butyl-3-hydroxy-2,6-dimethylbenzyl)-1,3,5-triazin-2,4,6 (1H, 3H, 5H)-trione, bis (4-tert.-butyl-3-hydroxy-2,6-dimethylbenzyl)dithiolterephthalate, tris(3,5-ditert.-butyl-4-hydroxybenzyl) isocyanurate, the triester of β-(4-hydroxy-3,5-ditert.-butylphenyl) propionic acid with 1,3,4-tris-(2-hydroxyethyl)-5-triazin-2,4,6 (1H, 3H, 5H)-trione, bis[3,3-bis-(4′-hydroxy-3-tert.-butylphenyl)-butyric acid] glycol ester, 1,3,5-trimethyl-2,4,6 tris-(3,5-ditert.-butyl-4-hydroxy-benzyl) benzene, 2,2′-methylene-bis-(4-methyl-6-tert.-butylphenyl) terephthalate, 4,4-methylene-bis-(2,6-ditert.-butylphenol), 4,4′-butylidene-bis-(tert.-butyl-metacresol), 2,2′-methylene-bis-(4-methyl-6-tert.-butyl-phenol.

Sulphur-containing antioxidative co-stabilizers which may be used include for example distearylthiodipropionate, dilaurylthiodipropionate, methane tetrakis (methylene-3-hexylthiopropionate), methane tetrakis (methylene-3-dodecylthiopropionate) and dioctadecyldisulphide. Phosphorus-containing co-stabilizers include for example trinonylphenyl phosphite, 4,9-distearyl-3,5,8,10-tetraoxadiphosphaspiroundecane, tris(2,4-ditert.-butylphenyl)phosphite and tetrakis (2,3-ditert.-butylphenyl)-4,4′-biphenylylene diphosphonite. Further additives such as aminoaryl compounds and U.V.- absorbers and light stabilizers e.g. 2-(2'-hydroxyphenyl)-benzotriazole, 2-hydroxybenzophenone, 1,3-bis-(2'-hydroxybenzoyl)benzene, salicylates, cinnamates, benzoates and substituted benzoates, sterically hindered amines and oxalic acid diamides may be used. Other known types of additives, e.g. flame retardants and antistatic agents, may also be added.

Preferably a compound of formula VI

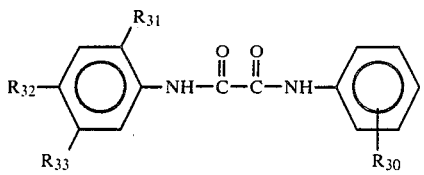 (VI)

in which $R_{30}$ is $C_{6-22}$alkyl or $C_{6-22}$alkoxy;

$R_{31}$ and $R_{32}$ independently, are selected from hydrogen, $C_{1-8}$alkyl, $C_{1-12}$alkoxy, $C_{1-12}$alkylthio, phenoxy and phenylthio provided that only one of $R_{31}$ and $R_{32}$ is alkylthio, phenoxy or phenylthio; and $R_{33}$ is hydrogen or $C_{1-8}$alkyl; is added to a compound containing one or more units of formula I.

The compounds of the invention can also be used in photopolymeric substrates containing photoinitiators for the photopolymerisation.

The compounds of formula I are especially suitable for use in organic polymer-containing coatings, particularly automotive finishes.

Automotive finishes are generally solutions or dispersions of organic polymers or polymer precursors in organic solvents. The majority are stoving finishes, which require the application of heat, generally above 80° C., in order to harden the finish in an acceptable time once it has been applied to the primer-coated metal surface. The hardening step may be accelerated by the use of an acid catalyst. The effect of this heating may be to accelerate the chemical reaction between polymer precursors in a thermosetting system, or to bring about fusion of particles of a thermoplastic polymer.

Many automotive finishes are metallic finishes, which contain flakes of metal, usually aluminium, in order to provide optical effects due to reflection. Such finishes are often two-coat finishes, in which a clear top coat finish is applied over a base coat finish containing a single pigment or metal flakes. The compounds of formula I can be in the top coat finish or the ground coat finish, preferably the former. Such two-coat metallic finishes have particular need of U.V.-stabilizers in the top coat, since the polymer in this coat is not protected by light-absorbing pigments, and it is subjected to almost double the normal amount of radiation because of reflection of light from the lower metallic layer.

The compounds of formula I are suitable for use as U.V.-stabilizers in a wide range of liquid finishes, for example those based on combinations of melamine-formaldehyde resins with oil-modified polyester resins, polyacrylate resins with added crosslinkers, or saturated polyesters; or on self-crosslinkers, or saturated polyesters; or on self-crosslinked polyacrylate or polyacrylate resin co-polymerised with styrene.

Further examples are two-component finishes based on an aliphatic or aromatic di-isocyanate and a hydroxy-group-containing polyacrylate, polyester or polyether resin. These polyurethane 2 component finishes are preferably hardened at 60° to 120° C. Thermoplastic polyacrylate resins may also be used, the latter being particularly useful in metallic finishes, as are also polyacrylate resins with added crosslinkers in combination with melamine-formaldehyde resins etherified with butanol and, further, hydroxy-group-containing polyacrylate resins hardened with aliphatic di-isocyanates. Such polyacrylate resins are described in U.S. Pat. No. 3,062,753, the contents of which are incorporated herein by reference.

The compounds of formula I are particularly useful in acid catalysed stoving finishes particularly in the top coat of two layer metallic finishes.

The compounds of formula I may be added to the finish at any stage in its manufacture, and may be added in solid form or in solution, preferably in the form of a liquid concentrate in a suitable solvent.

In practice the compounds of formula I are added to a finish as a solution in organic solvent (as a liquid finish) in which the binder material is between 35% (low solid finishes) and 70% by weight (high solid finishes). The binder material of the finish can be in aqueous emulsion or suspension form (as an aqueous finish) in which the binder material part makes up 20 to 30% by weight. However, the compounds of formula I can be added to known powder finishes.

The compounds of formula I are to be added to the liquid or powder finishes before stoving or hardening. Preferably the compounds of formula I are used in liquid finishes since it is easy to add exact dosages. It is particularly preferred to use a concentrate (preferably in a hydrocarbon solvent) containing at least 40% preferably 60 to 80% by weight of the total weight of the concentrate of a compound of formula I to introduce the compound of formula I to finishes for stoving.

The addition of from 0.01 to 8% by weight, preferably 0.2 to 4% by weight of one or more compounds of formula I gives a clear improvement in the light- and weather-stability of organic pigments in stoving finishes as well as reducing the tendency to hairline cracking and loss of gloss as the result of weathering. This is also found for metallic finishes and excellent long-term stability of the clear top coat of two layer metallic finishes is obtained. In such finishes, the compound of formula I may be added to the metallic undercoat, the clear top coat or both, preferably only to the clear top coat. The metal surface to be finished may be under-coated with primer coatings as is customary in the art of coating metal surfaces.

The invention will now be illustrated by the following Examples in which all parts and percentages are by weight and all temperatures are in °C. unless indicated to the contrary.

EXAMPLE 1

13.0 g of 2,2,6,6-tetramethyl-4-benzoyloxypiperidine together with 7.0 g of triethylamine are dissolved in 50 ml of chloroform and to this mixture 6.8 g of oxalic acid monoethylester chloride dissolved in 10 ml of chloroform is added at −16° over 1 hour. The mixture is stirred for a further 2½ hours at −15° and then is diluted in 60 ml of hexane and is then washed 3 times with 200 ml of water. The organic phase is dried and the solvent is distilled off. The residue is stirred with isopropanol. The product that precipitates is filtered and the isopropanol solvent is distilled off. The residue is purified using FLASH chromatography. (Solvent Toluene/Acetone 9:1 Column Silica Gel 60 Merck 9385).

A viscous light yellow oil of the formula 1a

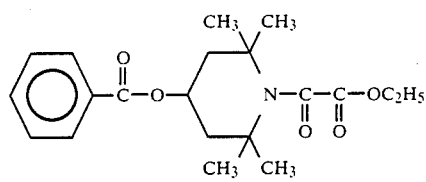
(1a)

results.

EXAMPLE 2

13.5 Parts of a compound of formula 2a

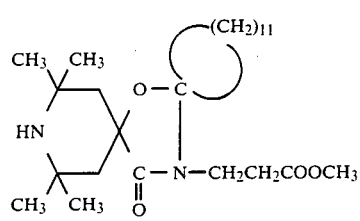
(2a)

and 5.05 g of triethylamine are added to 70 ml of chloroform. To the solution 8.19 g of oxalic acid monoethylester chloride in 10 ml chloroform is added at 17° over 1 hour and then allowed to react for a further 5 hours at −17°. To the resulting clear solution, 160 ml of hexane are added at 0° and the resulting hydrochloride is filtered off. The organic solution is washed at neutral pH, dried, and the solvent is distilled off. 14.0 g of a clear yellow resin results having the formula 2b

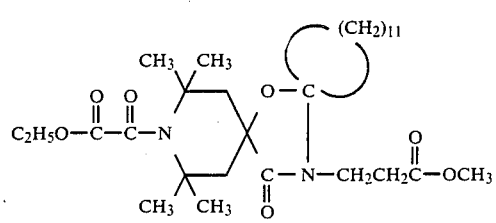
(2b)

This can be purified using chromatography and then isolated. (Column silica gel-60 Merck 9385-solvent Toluene/acetone [9:1].

EXAMPLES 3 to 10

In a manner analogous to that of Examples 1 or 2 products of the formula

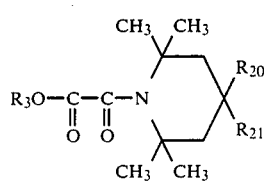

in which the symbols are defined in the Table below may be prepared from suitable reactants.

| No. | $R_3$ | $R_{20}$ | $R_{21}$ |
|---|---|---|---|
| 3 | $CH_3$ | H | $-O-\overset{O}{\underset{\|}{C}}-C_{17}H_{25}$ |
| 4 | $C_2H_5$ | H | $-O-\overset{O}{\underset{\|}{C}}-C_{17}H_{35}$ |
| 5 | $CH_3$ | H | $-O-\overset{O}{\underset{\|}{C}}-\underset{X}{\overset{X}{\text{C}_6H_2}}-OH$ |
| 6 | $C_2H_5$ | H | $-O-\overset{O}{\underset{\|}{C}}-\underset{X}{\overset{X}{\text{C}_6H_2}}-OH$ |
| 7 | $C_2H_5$ | H | $-\underset{\underset{CH_3}{\overset{\|}{C=O}}}{\overset{\|}{N}}-CH=CH-\overset{O}{\underset{\|}{C}}-OCH_3$ |
| 8 | $C_2H_5$ | H | $-\underset{\underset{CH_3}{\overset{\|}{C=O}}}{\overset{\|}{N}}-C_8H_{17}n$ |
| 9 | $CH_3$ | H | $-\underset{\underset{CH_3}{\overset{\|}{C=O}}}{\overset{\|}{N}}-C_8H_{17}n$ |
| 10 | $CH_3$ | H | $\underset{\underset{O}{\overset{\|}{C}}-N-C_{12}H_{25}}{\overset{H\ O}{\underset{\|\ \|}{N-C}}}\text{(X)}$ |
| 11 | $C_2H_5$ | H | $-O-\overset{O}{\underset{\|}{C}}-C_6H_4-t\text{-butyl}$ |

The symbol X is $-C(CH_3)_3$ in the above Table.

APPLICATION EXAMPLE A

A clear finish of
80 Parts of Viacryl SC 344 (a 50% solution of an acryl resin from Vianova),
13.9 Parts of Maprenal MF 80 (a 72% solution of a melamine resin from Hoechst) and
4.1 Parts of Byketol OK (from Byk-Malinckrodt)
is added to 2 parts of a compound of formula 1a (described in Example 1). After 1 minute the light stabiliser material so formed is dissolved in a finish. The finish is applied conventionally (according to the known 2 layer procedure) to a metallic or single pigment finish whilst still wet by spraying to form a layer having a thickness of 30 to 40 μm. The resulting coating is then hardened at 140° C. for 30 minutes. The coating shows very good resistance to U.V. light and weathering.

APPLICATION EXAMPLE B

A clear finish of 29.5 Parts of Setalux C-1502 XX-60 (a 60% solution of an acryl resin from Synthese B.V.),
39.2 Parts of Setalux C-1382 BX-45 (a 45% solution of an acryl resin from Synthese B.V.),
21.4 Parts of Setamine US-138 BB-70 (a 70% solution of a melamine resin from Synthese B.V.)
2.5 Parts of Baysilonoil [(2% solution in Xylene) from Bayer] and
7.4 Parts of Depanol Y (a solvent from Hoechst)
is stirred together with 2.5 parts of a compound of formula Ia (described in Example 1) and 2 parts of an acid catalyst derived from phosphoric acid (Type: Catalyst 296-9 from American Cyanamid) to form a homogeneous mixture. The finish is applied conventionally (according to the known 2 layer procedure) to a metallic or single pigment finish whilst both are still wet by spraying to form a layer having a thickness of 30 to 40 μm. The resulting coating is then hardened at 110° C. for 20 minutes. The coating shows very good resistance to U.V. light and weathering.

APPLICATION EXAMPLE C

A clear finish of

75 Parts Macrynal SH 510N (a hydroxy containing acryl resin from Bayer)
2 Parts of Baysilon-oil A [(1% solution in xylene) from Bayer]
0.3 Parts of dibutyl zinc dilaurate
0.35 Parts diethanolamine
5.0 Parts of ethylglycol acetate
5.0 Parts of Solvesso 100
6.0 Parts of Xylene and
6.35 Parts of butyl acetate
is added to 23.5 parts of a compound of formula Ia (described in Example 1) and 30 parts of Desmodur N 75 (from Bayer). The homogeneous mixture so formed is applied conventionally (according to the known 2 layer procedure) to a metallic or single pigment finish whilst both are still wet by spraying to form a layer having a thickness of 30 to 40 μm and the resulting coating is hardened over 20 minutes at 80° to 90° C. The resulting 2K-PUR coating shows a good resistance to U.V. light and weathering.

APPLICATION EXAMPLE D

A single white pigmented finish of 14.30 Parts of Setamine US-132 BB 70 (a 70% solution of a melamine resin from Synthese)
57.15 Parts of Setal 84 W-70 (a 70% solution of an alkyd resin from Synthese)
7.70 Parts of n-butanol
1.85 Parts of butylglycol acetate
9.50 Parts of Xylene and
25 Parts of titanium dioxide (Rutil type)
is added with 1.38 parts of the product of formula Ia (see Example 1). The finish is conventionally applied to a grounded steel metal to which a filler of layer thickness 20 to 30 μm has been annealed, by spraying and after standing for 30 minutes at room temperature the steel metal surface is annealed at 120° C. for 20 minutes. The resulting coating shows very good resistance to U.V. light and weathering.

In Application Examples A to D instead of the product of formula Ia, an appropriate amount of the product of any one of the other Examples 2 to 10 can be used.

What is claimed is:

1. A light stabilizer for polymeric materials, said stabilizer being of the formula $$R_3O-\underset{\underset{O}{\|}}{C}-\underset{\underset{O}{\|}}{C}-Q$$

wherein

Q is the residue of a piperidine light stabilizer which is attached to the $$-\underset{\underset{O}{\|}}{C}-$$

group at the nitrogen atom of a piperidine ring, which ring is unsubstituted in the 3- and 5-positions and substituted in the 2-position by two groups $R_1$ and in the 6-position by two groups $R_2$;

$R_1$ is $-CH_2C_{1-4}$alkyl or $-CH_3$ or both groups $R_1$ form $-(CH_2)_5-$;

$R_2$ is $-CH_2C_{1-4}$alkyl or $-CH_3$ or both groups $R_2$ form $-(CH_2)_5-$;

$R_3$ is furylmethyl, unsubstituted $C_{1-18}$alkyl; $C_{1-4}$alkyl monosubstituted by phenyl, the phenyl group of which is unsubstituted or substituted by 1 to 3 groups selected from $-OH$ and $C_{1-8}$alkyl; $C_{2-8}$alkyl monosubstituted by $C_{1-4}$alkoxy; phenyl, unsubstituted or substituted by 1 to 3 groups selected from $C_{1-8}$alkyl and $-OH$; or cyclohexyl, unsubstituted or monosubstituted by $C_{1-8}$alkyl or $-OH$.

2. A compound of formula II $$\left[R_3-O-\underset{\underset{O}{\|}}{C}-\underset{\underset{O}{\|}}{C}-N\underset{R_2\phantom{X}R_2}{\overset{R_1\phantom{X}R_1}{\diagup\!\!\!\diagdown}}O\right]_m R_4 \qquad (II)$$

in which $R_1$ is $-CH_2C_{1-4}$alkyl or $-CH_3$ or both groups $R_1$ form $-(CH_2)_5-$;

$R_2$ is $-CH_2C_{1-4}$alkyl or $-CH_3$ or both groups $R_2$ form $-(CH_2)_5-$;

$R_3$ is furylmethyl, unsubstituted $C_{1-18}$alkyl; $C_{1-4}$alkyl monosubstituted by phenyl, the phenyl group of which is unsubstituted or substituted by 1 to 3 groups selected from $-OH$ and $C_{1-8}$alkyl; $C_{2-8}$alkyl monosubstituted by $C_{1-4}$alkoxy; phenyl, unsubstituted or substituted by 1 to 3 groups selected from $C_{1-8}$alkyl and $-OH$; or cyclohexyl, unsubstituted or monosubstituted by $C_{1-8}$alkyl or $-OH$;

m is 1, 2, 3 or 4; and $R_4$, when m=1, is $C_{1-22}$alkyl; phenyl-$C_{1-4}$alkyl; $C_{1-4}$alkyl phenyl; $C_{1-21}$alkylcarbonyl; phenylcarbonyl; $C_{5-6}$cycloalkylcarbonyl; $C_{1-4}$alkyl-$C_{5-6}$cycloalkylcarbonyl; or phenyl $C_{1-6}$alkylcarbonyl in which the phenyl group can be substituted by 1 or 2 $C_{1-9}$alkyl groups and/or a hydroxyl group;

$R_4$, when m=2, is $C_{2-22}$alkylene; $C_{4-12}$alkenylene: xylylene, tolylene, phenylene or $-CO-R-CO-$ where R is a direct bond, $C_{1-6}$alkylene, $C_{2-6}$alkylene or phenylene unsubstituted or monosubstituted by $C_{1-4}$alkyl;

$R_4$, when m=3, is $$-CO-R'-CO- \\ \phantom{-CO-}\overset{|}{CO} \\ \phantom{-CO-R'-}|$$

where R' is $C_{1-12}$alkanetriyl; and
$R_4$, when m=4, is $+CO)_4R''$ where R'' is $C_{1-12}$-alkanetetrayl.

3. A compound of formula III $$\left[ R_3O-\underset{\underset{O}{\|}}{C}-\underset{\underset{O}{\|}}{C}-N \underset{R_2\ R_2}{\overset{R_1\ R_1}{\diagup\!\!\!\diagdown}} \overset{R_5}{N}-R_6 \right]_n \quad (III)$$

in which
$R_1$ is $-CH_2C_{1-4}$alkyl or $-CH_3$ or both groups $R_1$ form $-(CH_2)_5-$;
$R_2$ is $-CH_2C_{1-4}$alkyl or $-CH_3$ or both groups $R_2$ form $-(CH_2)_5-$;
$R_3$ is furylmethyl, unsubstituted $C_{1-18}$alkyl; $C_{1-4}$alkyl monosubstituted by phenyl, the phenyl group of which is unsubstituted or substituted by 1 to 3 groups selected from $-OH$ and $C_{1-8}$alkyl; $C_{2-8}$alkyl monosubstituted by $C_{1-4}$alkoxy; phenyl, unsubstituted or substituted by 1 to 3 groups selected from $C_{1-8}$alkyl and $-OH$; or cyclohexyl, unsubstituted or monosubstituted by $C_{1-8}$alkyl or $-OH$;
$R_5$ is hydrogen; $C_{1-2}$alkylcarbonyl; $C_{1-12}$alkyl; phenyl $C_{1-12}$alkyl phenylcarbonyl or phenyl $C_{1-8}$alkylcarbonyl in which the phenyl group of each phenyl-bearing $R_5$ group is unsubstituted or monosubstituted by $-OH$ or $C_{1-9}$alkyl or the phenyl group is substituted by one $-OH$ group and one or two $C_{1-4}$alkyl groups;
n is 1 or 2;
$R_6$, when n=1, is $C_{1-12}$alkyl, $C_{2-12}$alkenyl, $C_{5-6}$cycloalkyl or $-CH_2CH_2COOR_3$ where $R_3$ is as defined above or
$R_6$, when n=2, is $C_{2-12}$alkylene, phenylene, xylylene or tolylene.

4. A compound of formula IV $$\left[ R_3O-\underset{\underset{O}{\|}}{C}-\underset{\underset{O}{\|}}{C}-N \underset{R_2\ R_2}{\overset{R_1\ R_1}{\diagup\!\!\!\diagdown}} \overset{\overset{R_7}{|}}{\underset{\underset{O}{\|}}{\underset{C-N}{N-C=O}}}-R_6 \right]_n \quad (IV)$$

in which
$R_1$ is $-CH_2C_{1-4}$alkyl or $-CH_3$ or both groups $R_1$ form $-(CH_2)_5-$;
$R_2$ is $-CH_2C_{1-4}$alkyl or $-CH_3$ or both groups $R_2$ form $-(CH_2)_5-$;
$R_3$ is furylmethyl, unsubstituted $C_{1-18}$alkyl; $C_{1-4}$alkyl monosubstituted by phenyl, the phenyl group of which is unsubstituted or substituted by 1 to 3 groups selected from $-OH$ and $C_{1-8}$alkyl; $C_{2-8}$alkyl monosubstituted by $C_{1-4}$alkoxy; phenyl, unsubstituted or substituted by 1 to 3 groups selected from $C_{1-8}$alkyl and $-OH$; or cyclohexyl, unsubstituted or monosubstituted by $C_{1-8}$alkyl or $-OH$;
n is 1 or 2;
$R_6$, when n=1, is $C_{2-12}$alkyl, $C_{1-12}$alkenyl, $C_{5-6}$cycloalkyl or $-CH_2CH_2COOR_3$ where $R_3$ is as defined above; or
$R_6$, when n=2, is $C_{2-12}$alkylene, phenylene, xylylene or tolylene and
$R_7$ is hydrogen or $C_{1-12}$alkyl.

5. A compound of formula V $$R_3-\underset{\underset{O}{\|}}{C}-\underset{\underset{O}{\|}}{C}-N \underset{R_2\ R_2}{\overset{R_1\ R_1}{\diagup\!\!\!\diagdown}} \overset{\overset{R_9}{\diagdown}\underset{R_{10}}{\diagup}}{\underset{\underset{O}{\|}}{\underset{C-N}{O-C}}} \underset{R_{12}}{} \quad (V)$$

in which
$R_1$ is $-CH_2C_{1-4}$alkyl or $-CH_3$ or both groups $R_1$ form $-(CH_2)_5-$;
$R_2$ is $-CH_2C_{1-4}$alkyl or $-CH_3$ or both groups $R_2$ form $-(CH_2)_5-$;
$R_3$ is furylmethyl, unsubstituted $C_{1-18}$alkyl; $C_{1-4}$alkyl monosubstituted by phenyl, the phenyl group of which is unsubstituted or substituted by 1 to 3 groups selected from $-OH$ and $C_{1-8}$alkyl; $C_{2-8}$alkyl monosubstituted by $C_{1-4}$alkoxy; phenyl, unsubstituted or substituted by 1 to 3 groups selected from $C_{1-8}$alkyl and $-OH$; or cyclohexyl, unsubstituted or monosubstituted by $C_{1-8}$alkyl or $-OH$;
$R_9$ and $R_{10}$, independently of one another, are hydrogen, $C_{1-30}$alkyl or benzyl; or
$R_9$ is hydrogen or $C_{1-4}$alkyl and $R_{10}$ is phenyl, $C_{1-4}$alkylphenyl, chlorophenyl, 4-hydroxy-3,5-ditert.-butylphenyl or naphthyl; or
$R_9$ and $R_{10}$ together with the C-atom to which they are attached form either a $C_{5-15}$cycloalkylidene ring, unsubstituted or substituted by a $C_{1-4}$alkyl group, or a group of formula (b)

$$R_a-N \underset{R_2\ R_2}{\overset{R_1\ R_1}{\diagup\!\!\!\diagdown}} C \diagdown \quad (b)$$

where $R_1$ and $R_2$ are defined above and
$R_a$ is hydrogen, $C_{1-8}$alkyl, $$-\underset{\underset{O}{\|}}{C}-R_{13},$$

cyanomethyl or $$-\underset{\underset{O}{\|}}{C}-\underset{\underset{O}{\|}}{C}-O-R_3;$$

$R_{12}$ is hydrogen or

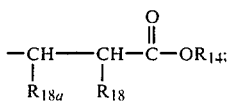

$R_{13}$ is $C_{1-6}$alkyl, phenyl, —O—$C_{1-4}$alkyl or —$NR_{15}R_{16}$;

$R_{14}$ is hydrogen, a $C_{1-21}$alkyl or $C_{2-22}$alkenyl group which may be unsubstituted or monosubstituted by phenyl or naphthyl and which may be interrupted by —NH—, oxygen or by a $C_{1-4}$alkylimine group; phenyl; ($C_{1-12}$alkyl)phenyl; $C_{5-12}$cycloalkyl or $C_{2-20}$alkyl uninterrupted or interrupted by —NH— or oxygen or by a $C_{1-4}$alkylimine group and which alkyl group is substituted by 1 to 3 groups of formula (a) defined below and/or $C_{1-21}$alkylcarbonyloxy groups; or $C_{2-20}$alkenyl uninterrupted or interrupted by —NH— or oxygen or $C_{1-4}$alkylimine and which alkenyl group is substituted by 1 to 3 groups of formula (a) defined below and/or $C_{1-21}$alkylcarbonyloxy groups

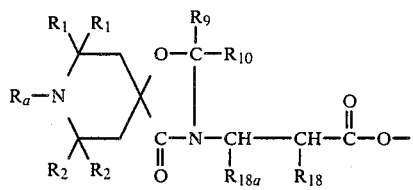

where $R_1$, $R_2$, $R_9$, $R_{10}$ and $R_a$ are defined above;

$R_{15}$ is hydrogen, $C_{1-12}$alkyl, $C_{5-6}$cycloalkyl, phenyl or $C_{1-12}$alkyl phenyl;

$R_{16}$ has a significance of $R_{15}$, independently of $R_{15}$, other than hydrogen; or $R_{15}$ and $R_{16}$ together with the N-atom to which they are attached form a 5- to 7-membered ring that may contain an —O-atom additionally;

$R_{18}$ is hydrogen or methyl; and $R_{18a}$ is hydrogen, methyl, phenyl or

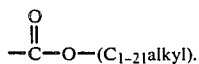

6. A compound according to claim 2 wherein $R_3$ is $C_{1-14}$alkyl, phenyl or benzyl.

7. A compound according to claim 2 wherein m is 1 or 2.

8. A compound according to claim 3 wherein $R_3$ is $C_{1-14}$alkyl, phenyl or benzyl.

9. A compound according to claim 3 wherein any phenyl group in $R_5$ is p-t-butylphenyl, p-nonylphenyl, 3,5-di-t-butyl-4-hydroxyphenyl or unsubstituted phenyl.

10. A compound according to claim 4 wherein $R_3$ is $C_{1-14}$alkyl, phenyl or benzyl.

11. A compound according to claim 4 wherein $R_7$ is methyl or ethyl.

12. A compound according to claim 5 wherein $R_3$ is $C_{1-14}$alkyl, phenyl or benzyl.

13. A compound according to claim 5 wherein $R_9$ and $R_{10}$ together with the C-atom to which they are attached form a $C_{5-15}$cycloalkylidene ring or a group of formula (b);

$R_{14}$ is $R'_{14}$ where $R'_{14}$ is $C_{1-12}$alkyl uninterrupted or interrupted by oxygen or an —NH— group, $C_{2-12}$alkenyl uninterrupted or interrupted by oxygen or —NH—, $C_{5-6}$cycloalkyl, phenyl $C_{1-4}$alkyl, phenyl or $C_{1-12}$alkylphenyl or a group of formula (c) to (l) below to whose free valencies further groups (a) and/or $C_{1-21}$alkylcarbonyloxy are attached;

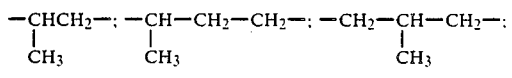

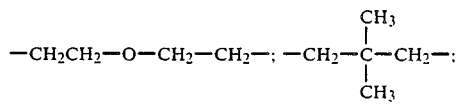

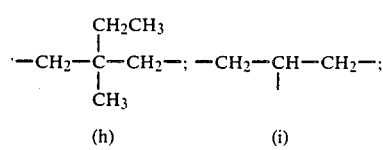

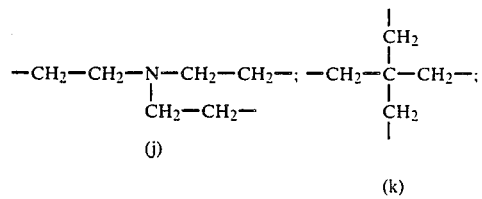

$+CH_2\!\!\rightarrow_p$
where p = 2–10;

(l)

and where $R_{15}$ and $R_{16}$ together with the N-atom to which they are attached form a 5- to 7-membered ring, said ring is a piperidine or morpholine ring.

14. A compound according to claim 6 wherein m is 1 or 2.

15. A compound according to claim 9 wherein $R_3$ is $C_{1-14}$alkyl, phenyl or benzyl.

16. A compound according to claim 10 wherein $R_7$ is methyl or ethyl.

17. A compound according to claim 13 wherein $R_3$ is $C_{1-14}$alkyl, phenyl or benzyl.

18. A compound according to claim 14 wherein $R_1$ and $R_2$ are all —$CH_3$.

19. A compound according to claim 14 wherein m is 1 and $R_4$ is $R'_4$ where $R'_4$ is phenylcarbonyl, t-butylphenylcarbonyl, p-t-butylphenyl, $C_{15-19}$alkylcarbonyl, 3,5-di-t-butyl-4-hydroxyphenylethyl or 3,5-di-t-butyl-4-hydroxyphenylcarbonyl or m is 2 and $R_4$ is $R'_4$ where $R'_4$ is $+CH_2\!\!\rightarrow_8$.

20. A compound according to claim 15 wherein $R_1$ and $R_2$ are all —$CH_3$.

21. A compound according to claim 16 wherein $R_1$ and $R_2$ are all —$CH_3$.

22. A compound according to claim 17 wherein $R_1$ and $R_2$ are all —$CH_3$.

23. A compound according to claim 17 wherein $R_9$ and $R_{10}$ together with the C-atom to which they are attached form cyclopentylidene, cyclohexylidene or cyclododecylidene.

24. A compound according to claim 19 wherein $R_1$ and $R_2$ are all —$CH_3$.

25. A compound according to claim 23 wherein $R_1$ and $R_2$ are all —$CH_3$.

26. A compound according to claim 20 wherein $R_3$ is $C_{1-4}$alkyl.

27. A compound according to claim 21 wherein $R_3$ is $C_{1-4}$alkyl.

28. A compound according to claim 24 wherein $R_3$ is $C_{1-4}$alkyl.

29. A compound according to claim 25 wherein $R_3$ is $C_{1-4}$alkyl.

30. A compound according to claim 26 wherein $R_3$ is methyl or ethyl, $R_5$ is methylcarbonyl, $R_6$ is n-octyl and n is 1.

31. A compound according to claim 27 wherein n is 1, $R_3$ is methyl and $R_6$ is dodecyl.

32. A compound according to claim 28 wherein m is 1, $R_3$ is ethyl and $R'_4$ is phenylcarbonyl or t-butylphenylcarbonyl.

33. A compound according to claim 29 wherein $R_3$ is ethyl, $R_9$ and $R_{10}$ together with the C-atom to which they are attached form a cyclododecylidine ring and $R_{12}$ is —$CH_2CH_2COOCH_3$.

* * * * *